United States Patent [19]

Keane

[11] Patent Number: 4,932,779
[45] Date of Patent: Jun. 12, 1990

[54] COLOR MEASURING INSTRUMENT WITH INTEGRATING SPHERE

[75] Inventor: Thomas J. Keane, Gaithersburg, Md.

[73] Assignee: BYK Gardner, Inc., Silver Spring, Md.

[21] Appl. No.: 293,621

[22] Filed: Jan. 5, 1989

[51] Int. Cl.$^5$ ............................ G01J 3/08; G01J 3/42
[52] U.S. Cl. .................... 356/319; 356/323; 356/446; 356/236; 250/228
[58] Field of Search ............. 356/319, 323, 325, 326, 356/328, 236, 402, 405, 406, 407, 408, 425, 446–448; 250/227, 228

[56] References Cited

U.S. PATENT DOCUMENTS

| | | | |
|---|---|---|---|
| 3,874,799 | 4/1975 | Isaacs et al. | 356/402 |
| 4,060,327 | 11/1977 | Jacobowitz et al. | 356/328 |
| 4,247,202 | 1/1981 | Failes | 356/310 |
| 4,268,170 | 5/1981 | Flint | 356/334 |
| 4,375,919 | 3/1983 | Busch | 356/326 |
| 4,487,504 | 12/1984 | Goldsmith | 356/323 |

FOREIGN PATENT DOCUMENTS

| | | | |
|---|---|---|---|
| 2606675 | 9/1977 | Fed. Rep. of Germany | 356/448 |
| 2096347 | 10/1982 | United Kingdom | 356/319 |

*Primary Examiner*—F. L. Evans
*Attorney, Agent, or Firm*—Leydig, Voit & Mayer

[57] ABSTRACT

In a color measuring instrument, an integrating sphere is used to illuminate the sample and fiber optics are used to carry light diffusely reflected from the sample and from an interior wall of the sphere to a spectrometer. The transmitting ends of the fiber optic bundles are fixed in the housing of the spectrometer as entrance slits for the spectrometer, which includes a fixed grating and one or two arrays of photodetectors to detect the spectra dispersed by the grating from light received from the two transmitting ends.

16 Claims, 3 Drawing Sheets

COLOR MEASURING INSTRUMENT WITH INTEGRATING SPHERE

This invention relates to a color measuring instrument and more particularly to an instrument which makes use of an integrating sphere to provide uniform diffuse illumination of a sample and in which the light reflected from the sample is measured spectroscopically.

BACKGROUND OF THE INVENTION

When an integrating sphere is used to illuminate a sample in a color or reflectance measuring instrument, the integrating sphere receives light from a light source through an entrance port and the diffusely reflecting interior walls of the integrating sphere reflect the light in multiple reflections so that uniform diffuse illumination is provided over the interior wall surface of the integrating sphere. The integrating sphere is provided with a port designed to receive a sample, the color of which is to be measured. When a sample is positioned over the sample port, the surface of the sample will be illuminated with uniform diffuse illumination multiply reflected from the walls of the integrating sphere. An exit port located on the sphere opposite the sample port will receive diffusely reflected light from the sample and the light passing through the exit port is separated into narrow-wavelength-band components, the intensities of which are measured to determine the reflectance of the sample for each narrow band component. When a sample is placed over the sample port, the color and presence of the sample itself will cause a discoloration and a change in level of the uniform illumination over the interior of the sphere and there is a need to correct the measurements for this level change and discoloration. One way of providing this correction is to provide a second exit port on the sphere positioned to receive light reflected from the wall of the sphere. Since the wall of the sphere is white, the color and intensity of the light reflected from the wall of the sphere when divided into its spectral components and measured will provide data for correcting the color measurement made from the sample.

In U.S. Pat. No. 4,487,504 of Herbert Goldsmith, there is disclosed a system which provides an integrating sphere to illuminate a sample at a sample port and a monochronometer is provided to make measurements of the intensity of the spectral components of the diffusely reflected light. In this instrument, light passing through a sample beam exit port of the integrating sphere is carried by a fiber optic bundle cable to a mechanical fiber optic switching mechanism. A second fiber optic bundle receives light reflected from the wall of the sphere and passing through a reference beam exit port. The second fiber optic bundle at its transmitting end is also connected in the fiber optic beam switching mechanism, which can selectively position either fiber optic bundle cable to transmit through an entrance slit of the monochronometer. When the fiber optic beam switching mechanism is one position, the monochronometer will receive light from the sample and when the switching mechanism is in a second position, the monochronometer will receive light from the wall of the integrating sphere, so that measurements of the spectral components of both the light reflected from the sample and the light reflected from the integrating sphere wall may be made by the monochronometer. As described in the patent, the monochronometer is provided with a pivoted optical grating which disperses the light received through the entrance slit into its spectral components. As the optical grating is pivoted, the spectral components dispersed by the grating are scanned over an exit slit of the monochronometer. A photodetector is positioned to receive the light passing through the exit slit and thus provide measurements of the intensity of the spectral components. The measurements made by the photodetector when the monochronometer is receiving light from the wall of the integrating sphere are used to correct the measurements made by the photodetector when the monochronometer is receiving light from the sample.

The instrument of the above described patent provides an effective system for correcting for the discoloration and level change of the illumination of the interior of the sphere as a result of a sample being positioned over the sample port. However, in order for the measurements to be accurate, the transmitting ends of the fiber optic bundle must be precisely aligned with the entrance slit of the monochronometer each time the beam switching mechanism is operated and must always be aligned to point its transmitting end in precisely the same direction each time a fiber optic bundle aligns with the entrance slit so that the light emitted from the bundle into the monochronometer is always emitted in the same direction from the bundle. As a result, the mechanical fiber optic switching mechanism must be very precisely made and it must maintain its operating precision through the repeated switching actions that occur during use. Wear in the mechanism cannot be permitted to interfere with the operating precision required.

In addition, because the above described instrument of the patent employs a monochronometer with a pivoting grating, in order to measure the entire spectrum, the instrument must take time for the grating to pivot and scan the entire spectrum past the entrance slit. This scanning must be done at least once for the sample, then the beam switching mechanism operated and then done at least once for the reference beam. Each scan by the optical grating takes about seven seconds.

SUMMARY OF THE INVENTION

The present invention improves over the above described system of the prior art in that it provides fiber optics to simultaneously transmit both the beam from the sample and the reference beam received from the integrating sphere to a spectrometer without the need of a switching mechanism. In the spectrometer, a fixed optical grating is provided which disperses the light from the sample or from the wall of the integrating sphere separately or simultaneously into spectral components and then measures the spectral components with an array of photodetectors mounted within the housing of the spectrometer. In accordance with the invention, as in the above mentioned Goldsmith U.S. Pat. No. 4,487,504, a first fiber optic bundle is positioned to receive light diffusely reflected from the sample through the sample beam port and a second fiber optic bundle is positioned to receive light from the wall of the integrating sphere diffusely reflected through the reference beam port. The transmitting ends of the two fiber optic bundles are mounted in a fixed position to illuminate the grating of the spectrometer. The system is adapted so that the spectrometer measures the spectra dispersed from the light received from the two fiber optic bundles separately.

In accordance with one embodiment of the invention, the transmitting ends of the two bundles are combined into a common transmitting end shaped into the form of an entrance slit for the spectrometer. Shutters operating in synchronism are provided between the integrating sphere and the two fiber optic bundles so that the entrance slit of the spectrometer receives light from only one of either the sample port or the reference port at any given instant of time.

In accordance with a second embodiment, the two fiber optic bundles are arranged in two entrance slits side by side in the spectrometer separated by the width of one entrance slit, which corresponds to the width of one photodetector in the array positioned to measure the dispersed spectral components. A shutter alternately blocks the light transmitted from the two fiber optic bundles into the spectrometer.

In accordance with a third embodiment, the two fiber optic bundles are arranged into two entrance slits leading into the photodetector positioned linearly one above the other and above and below a plane bisecting the grating. Two arrays of photodetectors are provided within the housing of the spectrometer each positioned to receive the light dispersed by the grating from one of the two entrance slits. Because of the positioning of the entrance slits and the arrays of photodetectors, each array of photodetector will receive the spectral components from only one of the fiber optic bundles.

The spectral components measured by the photodetector array from the light diffusely reflected by the sphere wall through the reference port will provide a measurement for each spectral component to correct the reflectivity measurement made for the corresponding spectral component from the light received from the sample in essentially the same manner as that described in the above mentioned patent.

In accordance with a further feature of the invention, fiber optics are employed to illuminate the integrating sphere. Light from the source is directed into a fiber optic bundle which is divided into four transmitting ends distributed around the circumference of the sphere and mounted to illuminate the interior of the sphere. In this manner, the direct illumination of the sphere interior wall is spread over a large area and the high intensity illuminated spot on the interior sphere wall that occurs when the sphere is illuminated through a single aperture is avoided.

DESCRIPTION OF THE PREFERRED EMBODIMENTS

Figure 1:
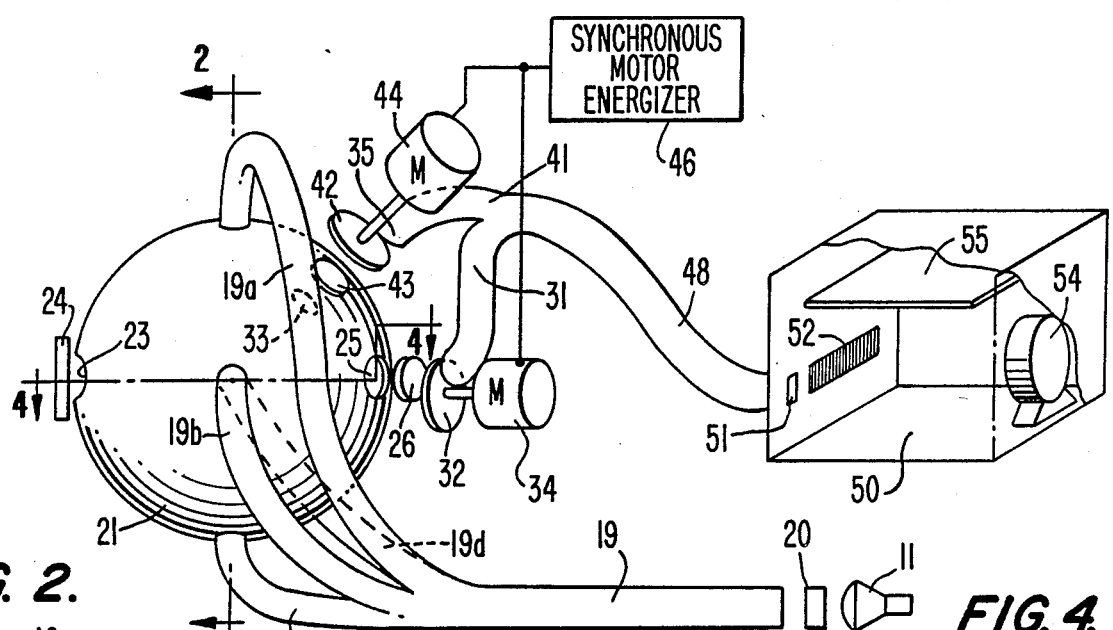
FIG. 1 schematically illustrates an embodiment of the invention.
Figure 2:
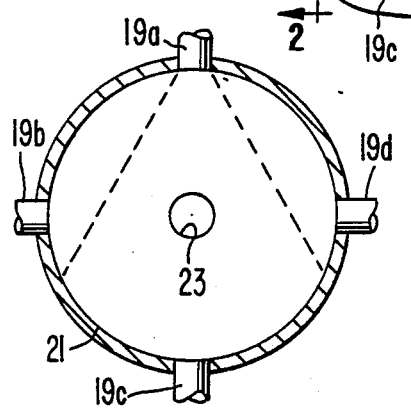
FIG. 2 is a sectional view through an integrating sphere in the embodiment of FIG. 1 taken along line 2—2 in FIG. 1.
Figure 3:
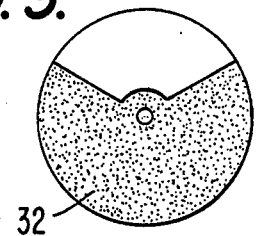
FIG. 3 illustrates a rotating shutter disk employed in the embodiment of FIG. 1.
Figure 4:
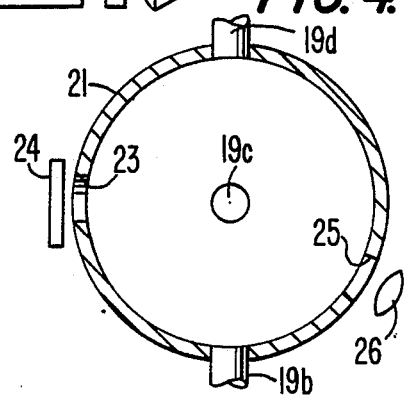
FIG. 4 is a sectional view through the integrating sphere of FIG. 2 taken along line 4—4 in FIG. 2.

In the embodiment as shown in FIG. 1, a light source 11 directs a beam of white light through a heat-absorbing filter 20 into the entrance end of a fiber optic bundle 19, which is divided into four transmitting ends 19a through 19d. These transmitting ends are mounted in the wall of an integrating sphere 21 to illuminate the interior of the sphere and are distributed at equal angles around a great circle of the sphere 21. The interior wall of the sphere has a high reflectance matte surface and the light beam entering the sphere from the transmitting ends 19a-19d is reflected through a series of reflections by the interior wall of the sphere so that diffuse radiation of uniform intensity is provided over the interior wall surface of the integrating sphere. Because the light is transmitted into the sphere through fiber optic bundles, the light upon entering the sphere will spread through an angle of 30 degrees from each transmitting end. As a result, the direct illumination of the interior surface of the sphere is spread over a relatively large area. This feature helps achieve more uniform illumination over the interior surface of the integrating sphere. A sample port 23 is defined in the sphere wall displaced 90 degrees on the sphere from the transmitting ends 19a-19d to receive a sample 24 to be analyzed or alternatively to receive a standard sample. The integrating sphere will irradiate the sample placed over the sample port 23 with uniform diffuse radiation. A sample beam port 25 is defined in the sphere wall opposite from the sample port 23 at an angle of eight degrees from normal to the plane of the sample port so that light diffusely reflected from the sample 24 at an angle of eight degrees will radiate through the exit port 25. An additional port, not shown, called a specular port, may be located eight degrees from normal to the sample port 23 directly on the opposite side from the exit port 25 so that light radiated to the sample from the specular port and specularly reflected by a sample at the sample port would be radiated through the sample beam exit port 25. The specular port may be either closed by a wall finish having the same finish as the interior of the sphere or by a black cavity entrance. If the specular port is closed by a black cavity, this will mean that the light radiated through the exit port 25 will contain no specular component. If the specular port is closed by the matte wall finish, then the light transmitted through the exit port 25 will contain a specular component reflected by the sample. The entrance end 29 of a fiber optic bundle 31 is positioned opposite the exit port 25 and a lens 26 focuses the light reflected by the sample 24 and radiated through the exit port 25 on the entrance end 29. Between the entrance end 29 and the lens 26 is a rotatable disk 32 driven by a motor 34. The disk 32 as shown in FIG. 3 is opaque over two thirds of its surface and transparent over the remainder of the surface so that when the disk 32 is rotated by the motor, it alternately blocks light passing through the exit port 25 or transmits the light to the entrance end 29 of the fiber optic bundle 31.

A second port 33, called a reference beam port, is positioned in the sphere wall to receive diffusely reflected light from the opposite interior wall of the sphere. Light diffusely reflected from the opposite interior wall will pass through the reference beam port 33 to the entrance end 35 of a fiber optic cable 41 through a focusing lens 43. The port 33, the lens 43 and the entrance end 35 of the fiber optic bundle 41 are arranged so that the entrance 35 is shielded from the sample port 23 and excludes any direct radiation from the sample 24 placed over the sample port 23. The reference beam port 33 must also be located in a position where it does not receive any radiation directly from the transmitting ends 19a and 19b. This is achieved by locating the reference beam port 33 displaced 45 degrees from the great circle on which the transmitting ends 19a–19d are located and half-way between a pair of the transmitting ends 19a and 19b. This location for the reference beam port 33 is outside the 30 degree beam spread from each of the transmitting ends 19a through 19d. Between the lens 43 and the entrance end 35 of the fiber optic bundle 41 is a rotatable disk 42 driven by a motor 44. The disk 42 like the disk 32 is one-third transparent and two-thirds opaque as shown in FIG. 3 so that as it is rotated by the motor 44, it alternately blocks the light passing through the exit port 33 or transmits the light to the entrance end 35 of the fiber optic cable 41. The motors 34 and 44 are synchronous motors and are energized by a source 46 to rotate discs 32 and 42 in synchronism so that when the disk 32 is transmitting light to the entrance end 29 of the fiber optic bundle 31, the disk 42 is blocking the light transmitted through the exit port 33 and vice versa and so that for one-third revolution of each disc, both discs will be blocking the light from the integrating sphere.

The fibers in the bundles 31 and 41 are combined into a single bundle 48 which leads to a spectrometer 50. Thus, the transmitting ends of the bundles 31 and 41 are combined into a common transmitting end 51, which is formed into the shape of an entrance slit for the spectrometer 50. The optic fibers of both of the bundles 31 and 41 are uniformly distributed over the transmitting end 51. The spectrometer 50 is similar to the spectrometer disclosed in U.S. patent application Ser. No. 868,700, filed May 30, 1986 and invented by the inventor of this application. Within the spectrometer 50 there is mounted a fixed optical grating 54, which is positioned to be illuminated with the light emitted from the transmitting end 51 of the fiber optic bundle 48 and disperse this light into its spectral components in a spectrum extending over an array of photodetectors 52. Each of the photodetectors 52 is rectangular in shape and has a width equal to 10 nanometers in wavelength in the spectrum as distributed over the array 52. Thus, each photodetector in the array 52 will detect a 10 nanometer component from the light received through the fiber optic bundle 48. In the specific embodiment of the invention there are 35 photodetectors arranged contiguously to detect a spectrum having wavelengths extending from 380 nanometers to 720 nanometers.

Figure 5:
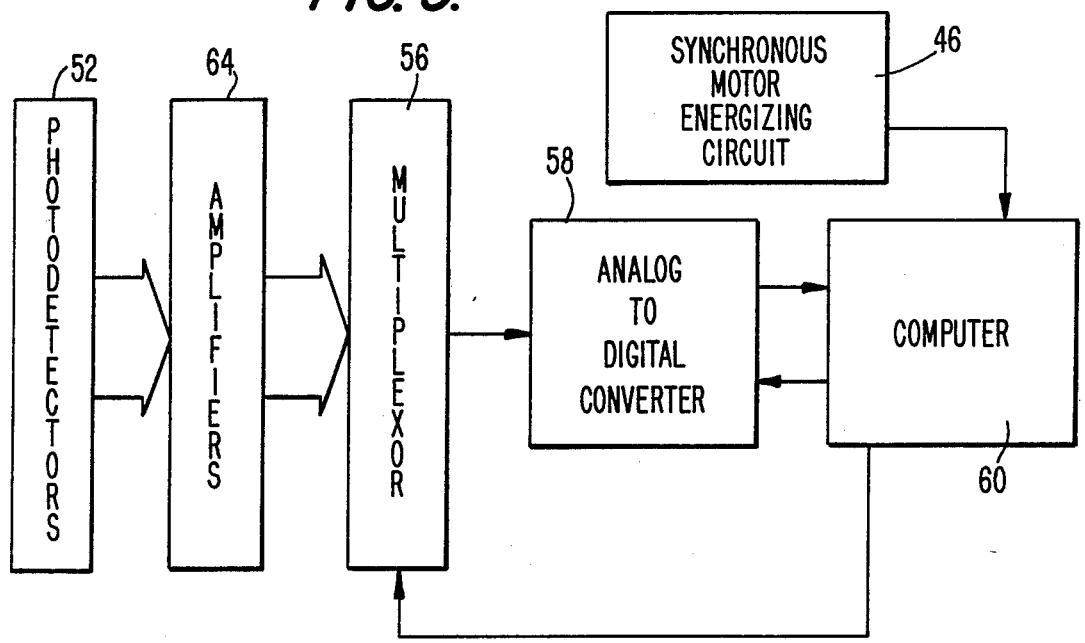
FIG. 5 is a block diagram of the electronics employed in the embodiment of FIG. 1.

As in the above mentioned copending application Ser. No. 868,700, the output signals from the photodetectors 52 are severally amplified by a set of amplifiers which are mounted on a circuit board 55 within the housing of the spectrometere 50. In FIG. 5, these amplifiers are designated by reference number 64. The outputs from the amplifiers are applied to a multiplexor 56 which applies the output signals from the amplifiers 64 one at a time in sequence to an analog to digital converter 58. The analog to digital converter converts each applied amplifier output to a digital value and applies it to a computer 60. The computer 60 controls the multiplexor 56 and the analog to digital converter 58 to read out the photodetector outputs when the transparent portion of the disk 32 is between the sample exit port 25 and the photodetector 29 and sequences through the entire set of photodetectors while the transparent portion of the disk 32 is in this position, so as read out of each 10 nanometer spectral component reflected from the sample 24 received by the spectrometer 50 is obtained. It takes 15 microseconds to read the output from a photodetector and convert it to a digital value so to obtain a digital reading from each of the entire array of 35 photodetectors takes 525 microseconds. When the disk 42 has its transparent portion between the reference beam exit port 33 and the entrance end 35 of the bundle 41, the computer again controls the multiplexor 56 and the analog to digital converter 58 to sequence through all of the photodetectors 52 in the array and obtain an additional output from each photodetector. The same readings are then obtained in the same manner from the photodetectors 52 by the computer 60 while the light passing through both ports 25 and 33 are blocked by opaque portions of the corresponding disks 32 and 42 to obtain dark period readings. All three readings can be obtained in less than a second. The readings thus obtained are then used to compute the reflectivity of a sample in each 10 nanometer component of the reflected spectrum in accordance with the equations disclosed in U.S. Pat. No. 4,487,504. The synchronous motor energizing circuit 46 applies a signal to the computer 60 indicating the position of the disks 32 and 33 so that the computer 60 in response to the received signal from the motor energization 46 is able to control the multiplexor 56 and the analog to digital converter 58 to read the output signals from the photodetectors at the appropriate times.

Figure 6:
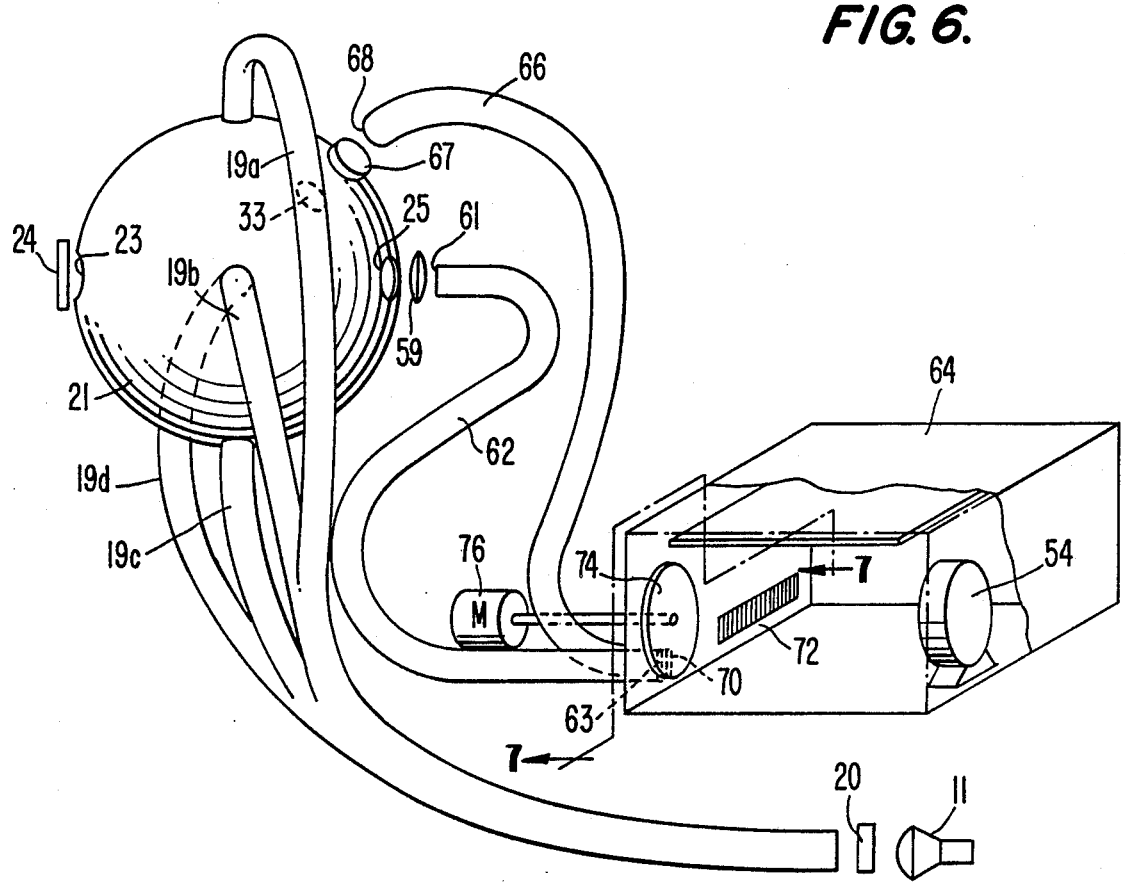
FIG. 6 illustrates a second embodiment of the invention.

The embodiment shown in FIG. 6 like the embodiment of FIG. 1 employs an integrating sphere 21 receiving light from a light source 11 introduced into the sphere through a fiber optic bundle 19 after passing through heat-absorbing filter 20. A sample port 23 is provided over which a sample 24 to be measured can be positioned. Also, as in the embodiment of FIG. 1, a sample beam port 25 is provided to transmit diffusely reflected light from the sample 24 and a reference beam port 33 is provided to transmit diffusely reflected light from the interior wall of the sphere 21. A lens 59 focusses light diffusely reflected from a sample and passing through the sample beam port 25 onto the entrance end 61 of a fiber optic bundle 62, which transmits the received light to a spectrometer 64. The transmitting end 63 of the fiber optic bundle 62 at the spectrometer 64 is formed into an entrance slit for the spectrometer 64. A lens 67 focusses light diffusely reflected from the opposite interior wall of the integrating sphere 21 and passing through the reference beam port 33 onto the entrance end 68 of a fiber optic bundle 66, which transmits the received light to the spectrometer 64. The fiber optic bundle 66 has a transmitting end 70 at the spectrometer 64 formed into an entrance slit for the spectrometer 64 positioned adjacent to the transmitting end 63 of the fiber optic bundle 62. Light emitted from either of the transmitting ends 63 or 70 is dispersed by the optical grating 54 into spectral components distributed over an array of photodetectors 72. The array of photodetectors 72 like the array 52 in the embodiment of FIG. 1 comprises a set of contiguous photodetectors each having a rectangular light receiving surface, each of which is 10 nanometers in width in a spectrum as distributed over the array. The transmitting ends 63 and 70 each have the same shape and size of one of the photodetectors in the array 72 and preferably the transmitting end 63 and 70 are separated by the width of one of the photodetectors 72. In other words, the center of the transmitting end 70 is displaced from the transmitting end 63 by an amount equal to the width of two photodetectors. As a result of the two transmitting ends being spaced by the width of two of the photodetectors in the array 72, the spectrum dispersed by the grating 54 from light received from the transmitting end 63 will be displaced from the spectrum dispersed from light received from the transmitting end 70 by the width of two photodetectors or in other words by 20 nanometers. It will be recalled that in the embodiment of FIG. 1, the array of photodetectors 52 has 35 photodetectors to measure a band width of 350 nanometers. In a preferred embodiment, the array 72 has 37 photodetectors which are organized in the two sets of 35 photodetectors counter from opposite ends of the array. The spectrum dispersed by the light received from the transmitting end 63, will be detected and measured by the 35 photodetectors on the left side of the array as shown in FIG. 6. The two photodetectors on the extreme right side of the array as shown in FIG. 6 will not be used in this measurement. The spectrum dispersed from light received from the transmitting end 70, will be measured by the 35 photodetectors on the right side of the array as viewed in FIG. 6. The two left most photodetectors will not be used to measure the spectrum dispersed from the light emitted by the transmitting end 70.

Figure 7:
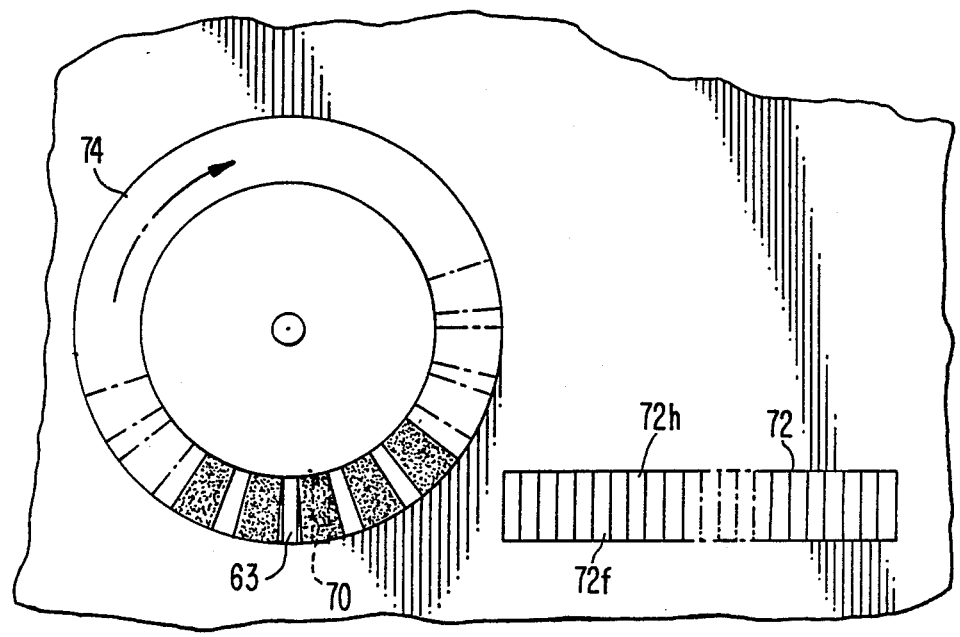
FIG. 7 is a sectional view of the spectrometer in FIG. 6 taken along line 7—7.

Inside the housing of the spectrometer 64 adjacent to the transmitting ends 63 and 70 of the fiber optic bundle 62 and 66 is a rotatable disk 74, which has a track around its outer periphery formed of alternate opaque and transparent segments, as best shown in FIG. 7. When the disk 74 rotates, the opaque segments alternately block the light from either the transmitting end 63 or the transmitting end 70 so that the array 72 receives light from only one of the transmitting ends 63 or 70 at a time. Also the pattern of the opaque and transparent segments is arranged so that in some angular positions of the disk 74 the light from both transmitting ends 63 and 70 is blocked so that as the disk rotates, first light from one of the two transmitting ends 63 and 70 is transmitted to the optical grating, then light from the other transmitting end is transmitted to the optical grating and then light from both transmitting ends is blocked, whereupon the sequence repeats. The disk 74 is rotated continuously through the sequence of positions by a stepping motor 76.

With the arrangement as described, the spectrum obtained from light emitted from the transmitting end 70 will be displaced 20 nanometers from the spectrum obtained from light emitted from the transmitting end 63. As a result, a given 10 nanometer component of the spectrum dispersed from light received from the sample will be detected by a different photodetector in the array 72 from the photodetector which detects the corresponding component in the spectrum dispersed from light received from the wall of the integrating sphere. For example as shown in FIG. 7, the photodetector 72f will detect a predetermined spectral component in the spectrum obtained from the sample 24 and will detect a different spectral component in the spectrum obtained from the wall of the sphere. The photodetector 72h which is positioned two photodetectors away from the photodetector 72f will detect the spectral component in the spectrum obtained from the wall of the sphere corresponding to the spectral component detected by the photodetector 72f obtained from the sample 24. Thus, when the correction of the reading obtained by the photodetector 72f is made by the computer in accordance with the light received from the wall of the sphere 21, it will use the reading obtained from the photodetector 72h to make the correction.

To obtain the necessary data to obtain the dark reading from the photodetectors, a read out from the photodetectors is taken each time both transmitting ends 63 and 70 are both blocked simultaneously by an opaque segment.

Figure 8:
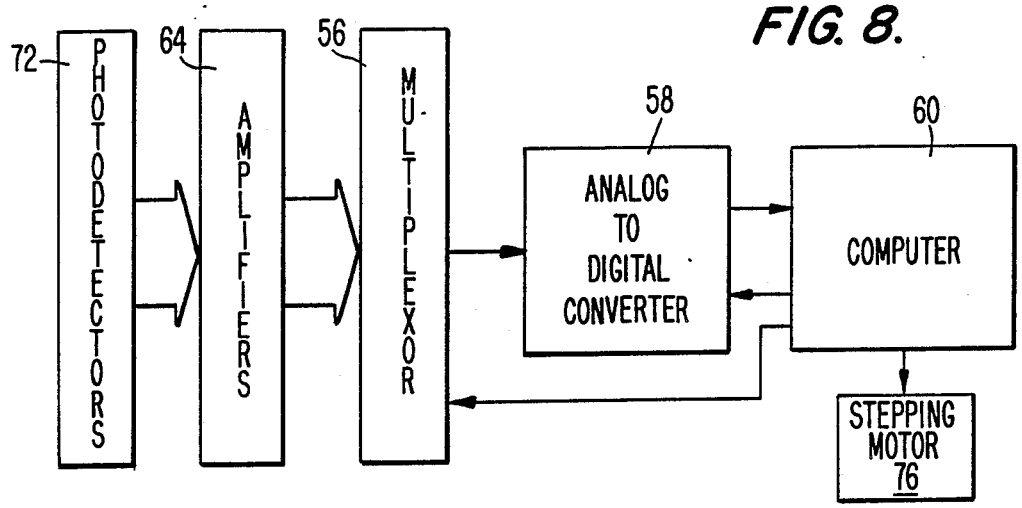
FIG. 8 is a block diagram illustrating the electronics employed in the system of FIG. 6.

As in the embodiment of FIG. 1, the output from the photodetectors of the array 72 are severally amplified by a set of amplifiers 64 and then the output from the amplifiers 64 are applied in sequence by a multiplexor 56 to the analog to digital converter 58, which converts each applied amplitude signal to a digital value and applies the digital value to a computer 60 where the digital value is stored, as shown in FIG. 8. The multiplexor 56 under the control of the computer 60 sequences through the entire array of photodetectors and the digital data is received by the computer each time the transmitting end 63 is opposite a transparent segment and again each time the transmitting end 70 is opposite a transparent segment in the disk 74. When both transmitting ends are blocked by an opaque segment, the multiplexor again sequences through the entire array of photodetectors to apply to the computer a digital value corresponding to the output from each photodetector when no light is received by the photodetector. These latter digital values are the dark values to be used in the computation of reflectance as described in U.S. Pat. No. 4,487,504. The computer 60 operates the stepping motor 76 in synchronism with the multiplexor 56 so that the photodetectors are read out in sequence at the appropriate times.

As an alternative to the embodiment of FIGS. 6 and 7, instead of using an array of 37 photodetectors, an array of 35 photodetectors could be used, in which case the end two 10 nanometer spectral components obtained from the light reflected from the wall of the sphere would not be measured as these components would fall beyond the end of the array of photodetectors. The measurements for the two missing 10 nanometer components, however could be calculated by extrapolating the values obtained from the 33 photodetectors in the array which would measure the spectrum from the wall of the sphere. Extrapolation provides sufficient accuracy, because the spectrum being measured is light being diffusely reflected from the white diffusely reflecting wall 21 which has a known reflectance.

Instead of employing a rotating shutter disk within the housing of the spectral photometer 64, synchronous rotating disks may be employed between the integrating sphere and receiving ends 61 and 68 of the fiber optic bundle 62 and 66 as in the embodiment of FIG. 1. With such an arrangement, the transmitting ends 63 and 70 could be positioned contiguously, in which case the offset of the two spectrums on the photodetector array would be only 10 nanometers instead of 20 nanometers.

Figure 9:
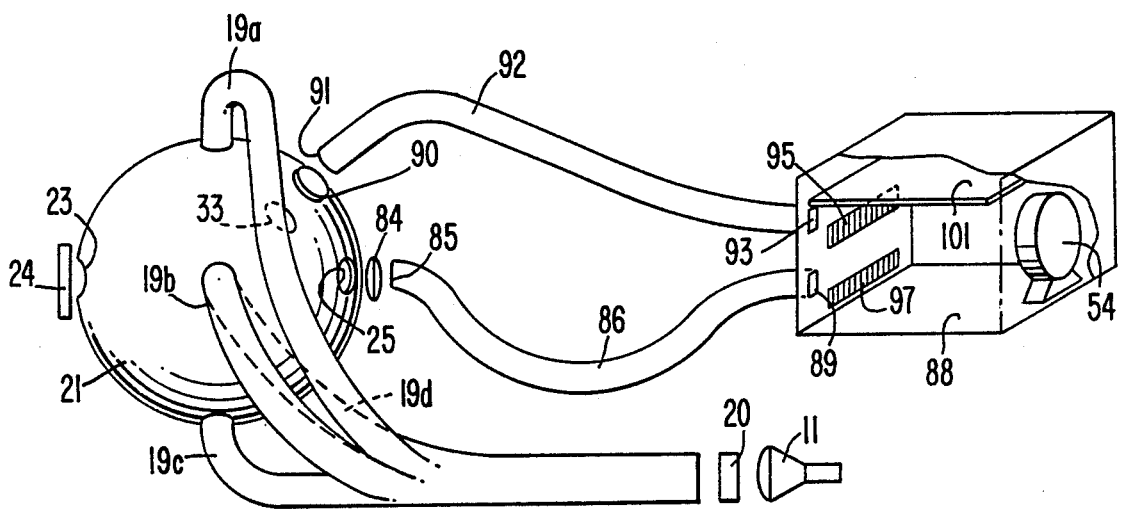
FIG. 9 illustrates a third embodiment of the invention.
Figure 10:
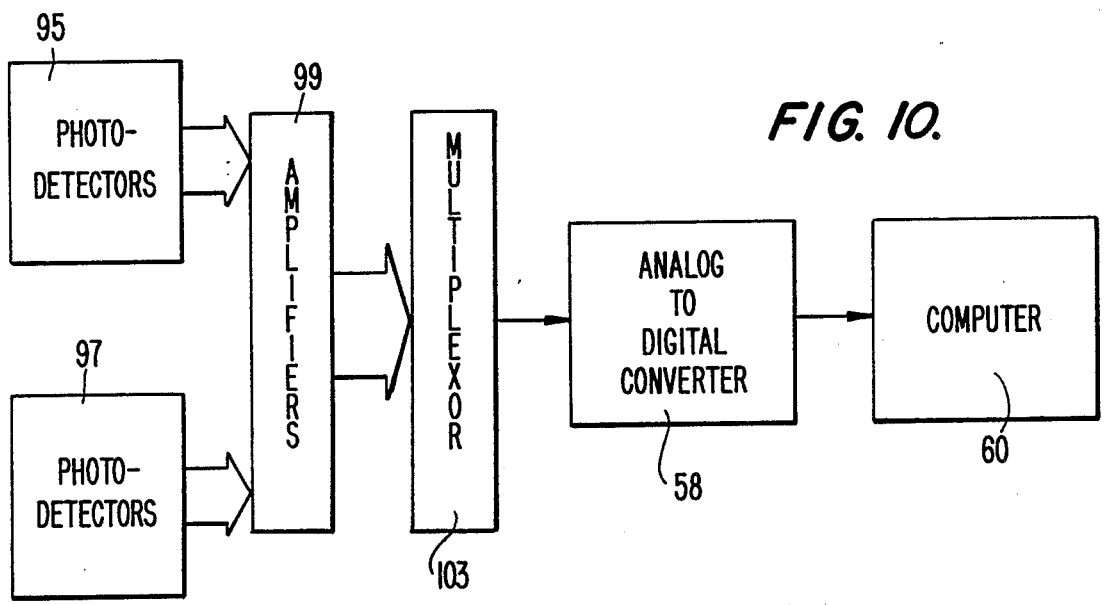
FIG. 10 is a block diagram illustrating electronics employed in the embodiment of FIG. 9.

In the embodiment of FIGS. 9 and 10, an integrating sphere 21 receiving light from a light source 11 through seat-absorbing filter 20 and fiber optics 19, is used to illuminate a sample 24 as in the embodiments of FIGS. 1 and 6. In this embodiment, light diffusely reflected from the sample 24 and passing through the sample beam port 25 is focused by lens 84 on the receiving end 85 of the fiber optic bundle 86 and transmitted to a spectrometer 88. The transmitting end 89 of the fiber optic bundle 86 is formed into the shape of a rectangular entrance slit in the spectrometer 88. Light diffusely reflected from the wall of the integrating sphere 21 passes through the reference beam port 33 and is focused by lens 90 on the receiving end 91 of a fiber optic bundle 92, which carries the received light to the spectrometer 88. The transmitting end 93 of the fiber optic bundle 92 is formed into the shape of a rectangular entrance slit 93 in the spectrometer 88. Light transmitted through the bundle 86 and emitted from the transmitting end 89 will illuminate and be dispersed by the fixed optical grating 54 of the spectrometer 88. Light travelling through fiber optic bundle 92 and emitted by the transmitting 93 will also illuminate and be dispersed by the optical grating 54. The transmitting ends 89 and 93 are spaced from one another and lie on opposite sides of a plane bisecting the grating 54 perpendicular to the grating lines. Ends 89 and 93 are separated by different distances from the bisecting plane. As a result, light received by the grating 54 from the transmitting end 89 will be dispersed into a spectrum above the bisecting plane where it will be detected by an array of photodetectors 95. Similarly, light received by the optical grating 54 from the transmitting end 93 will be dispersed into a spectrum below the plane bisecting the grating 54 where it will be received by an array of photodetectors 97. The array of photodetectors 95 and the spectrum detected by this array will be spaced above the bisecting plane by an amount equal to the amount that the transmitting end 89 is spaced below the bisecting plane. Similarly, the photodetector array 97 will be spaced below the bisecting horizontal plane by an amount equal to the amount that the transmitting end 93 is spaced above the bisecting plane. In this manner light from the sample 24 and from the wall of the sphere 21 are dispersed into two separate spectras simultaneously which can be simultaneously detected by the arrays 95 and 97. By having the entrance slits 89 and 93, and likewise the arrays 95 and 97, spaced different distances from the bisecting plane, interference from light inter-reflected between the grating and the detectors is avoided.

The signals generated by the photodetectors of the arrays 95 and 97, shown in FIG. 8, are simultaneously severally amplified by a set of amplifiers 99, which are mounted on a printed circuit board 101 within the spectrometer 88. The outputs from the amplifiers 99 are fed in sequence by a multiplexor 103 to an analog to digital converter 58 which converts each received value to a digital value and applies it to the computer 60 where each received value is stored for calculation of the reflectance value for each spectral component in the manner as described in the above mentioned patent. In this embodiment shutters, not shown, may be provided within the housing of the spectrometer 88 to periodically block light emitted from the transmitting ends 93 and 89 to provide dark value measurements. Alternatively, the shutters may be provided at the entrance ends 85 and 91 of the fiber optic bundles 86 and 92.

The above described instrument makes it possible to use an integrating sphere to illuminate the sample while at the same time provide for correction of the discoloration and level change of light within the sphere caused by the presence of the sample, and also make rapid and accurate measurements. The above description is of preferred embodiments of the invention and further modifications may be made in addition those described above, without departing from the spirit and scope of the invnetion which is defined in the appended claims.

What is claimed is:

1. A reflectance measuring instrument comprising an integrating sphere having an interior light reflecting wall including means for introducing light into said sphere and a sample port for receiving a sample, a sample beam port for receiving light diffusely reflected from a sample positioned at said sample port and a reference beam port for receiving light diffusely reflected from the interior wall of said sphere, a spectrometer including a housing and an optical grating mounted within said housing, a first fiber optic bundle having a receiving end for receiving light transmitted through the same sample beam port and a transmitting end mounted in a fixed position in said housing for illuminating said optical grating with light passing through said first fiber optic bundle, a second fiber optic bundle having an entrance end for receiving light transmitted through said reference beam port and a transmitting end mounted in a fixed position in said housing for illuminating said optical grating with light transmitted through said second fiber optic bundle, said optical grating dispersing light received from said first fiber optic bundle into a first spectrum and light received from said second fiber optic bundle into a second spectrum, and detecting means for detecting the intensity of spectral components of said first spectrum and spectral components of said second spectrum.

2. A reflectance measuring instrument as recited in claim 1 wherein the transmitting end of said first fiber optic bundle and the transmitting end of said second fiber optic bundle are combined into a common transmitting end for both fiber optic bundles in said housing, said instrument comprising shutter means for alternately blocking the light between said sample beam port and the entrance end of said first fiber optic bundle and between said reference beam port and the entrance end of said second fiber optic bundle.

3. A reflectance measuring instrument as recited in claim 2 wherein said optical grating is fixed within said housing and said detecting means comprises a fixed array of photodetectors mounted within said housing.

4. A reflectance measuring instrument as recited in claim 2 wherein said shutter means periodically simultaneously blocks the light between said sample beam port and the entrance end of said first optic bundle and between said reference beam port and the entrance end of said second fiber optic bundle.

5. A reflectance measuring instrument as recited in claim 1 wherein said optical grating is fixed within said housing and wherein said detecting means comprises at least one fixed array of photodetectors mounted within said housing.

6. A reflectance measuring instrument as recited in claim 1 wherein the transmitting ends of said first and second fiber optic bundles are displaced from one another so that said first and second spectra are not coextensive.

7. A reflectance measuring instrument as recited in claim 6 wherein said spectrometer includes first and second entrance slits disposed at the respective transmitting ends of said first and second fiber optic bundles, said first and second slits being disposed side by side in said housing parallel to each other, said instrument comprising means for alternately interrupting the light transmitted through said first and second fiber optic bundles.

8. A reflectance measuring instrument as recited in claim 7 wherein said means for alternately interrupting the light transmitted through said first and second fiber optic bundles periodically simultaneously interrupts the light through both said first and second fiber optic bundles.

9. A reflectance measuring instrument as recited in claim 7 wherein said detecting means comprises a multiplicity of uniform size rectangular photodetectors arranged contiguously in a linear array and wherein said first and second entrance slits are displaced from each other by an integer multiple of the width of one of said photodetectors.

10. A reflectance measuring instrument as recited in claim 7 wherein integer multiple is two.

11. A reflectance measuring instrument as recited in claim 8 wherein said means for alternately interrupting is mounted in said housing for blocking light between the transmitting ends of said first and second fiber optic bundles and said optical grating.

12. A reflectance measuring instrument as recited in claim 11 wherein said means for alternately interrupting is adapted to periodically block the light between both the transmitting ends of said first and second fiber optic bundles and said optical grating.

13. A reflectance measuring instrument as recited in claim 6 wherein the transmitting end of said first fiber optic bundle is positioned on a first side of a plane bisecting said optical grating perpendicular to the lines of said grating and the transmitting end of said second fiber optic bundle is positioned on a second side of said plane opposite to said first side and wherein said detecting means comprises first photodetecting means for detecting spectral components of said first spectrum positioned on said second side of said plane and second photodetecting means to detect the spectral components of said second spectrum positioned on said first side of said plane.

14. An optical instrument as recited in claim 13 wherein said optical grating is fixed within said housing and said first photodetecting means comprises an array of photodetectors within said housing on said second side of said plane and said second photodetecting means comprises an array of photodetectors within said housing on said first side of said plane.

15. A component of an instrument comprising a source of light, an integrating sphere, and fiber optics positioned to receive light from said source and to transmit the received light to the interior of said sphere, said fiber optics having a plurality of transmitting ends distributed around said sphere to directly illuminate different areas of the interior wall of said sphere with the light transmitted through said fiber optics.

16. A reflectance measuring instrument comprising a component as recited in claim 15 said integrating sphere having a sample port for receiving a sample and means for measuring the light diffusely reflected from a sample received at said sample port.

* * * * *